(12) United States Patent
Tosaki

(10) Patent No.: US 6,523,397 B1
(45) Date of Patent: Feb. 25, 2003

(54) CURING CHARACTERISTICS MEASURING APPARATUS AND MEASURING METHOD

(75) Inventor: Chikao Tosaki, Kawasaki (JP)

(73) Assignee: Nichigo Shoji Co., Ltd., Tokyo (JP)

( * ) Notice: Subject to any disclaimer, the term of this patent is extended or adjusted under 35 U.S.C. 154(b) by 0 days.

(21) Appl. No.: 09/499,396

(22) Filed: Feb. 7, 2000

(30) Foreign Application Priority Data

Feb. 8, 1999 (JP) .......................................... 11-030648

(51) Int. Cl.⁷ ............................ G01N 11/14; G01N 3/24
(52) U.S. Cl. .................... 73/54.39; 73/54.28; 73/54.41; 73/843; 73/54.29
(58) Field of Search ............................ 73/54.39, 54.29, 73/54.28, 54.35, 54.41, 843, 845, 866; 374/53

(56) References Cited

U.S. PATENT DOCUMENTS

| 3,681,980 A | * | 8/1972 | Decker ...................... 73/811 X |
| 4,584,882 A | * | 4/1986 | Tusuki ........................ 73/847 |
| 4,837,776 A | * | 6/1989 | Poll ........................ 73/813 X |
| 5,487,307 A | * | 1/1996 | Landsren et al. ............. 73/803 |

FOREIGN PATENT DOCUMENTS

| JP | 2-236141 A | * | 9/1990 | ................. 73/54.41 |
| JP | 5-2841 Y2 | | 1/1993 | |
| JP | 7-72710 B2 | | 8/1995 | |
| JP | 11-190690 A | * | 7/1999 | ........... G01N/11/14 |

OTHER PUBLICATIONS

Derwent Abstract of SU631588A, inventor Mekhtizad et al, Materials shear study electromagnetic oscillator—with A.C. and D.C. stimulation for torsional oscillator and inductive coil sensor located on same spindle, Acc–No. 1979–H0818B, Nov. 1978.*

* cited by examiner

Primary Examiner—Thomas P. Noland
(74) Attorney, Agent, or Firm—Oblon, Spivak, McClelland, Maier & Neustadt, P.C.

(57) ABSTRACT

A curing characteristics measuring apparatus in which a sample chamber having a fixed surface and a rotation-vibrating drive surface is charged with a sample having a viscoelasticity, a torsional vibration is applied to the sample through the drive surface, a shearing stress generated in the sample is observed as a torque through the fixed surface or the drive surface, wherein mechanism is provided for reducing volume of the sample chamber following volume contraction generated in curing process of the sample.

10 Claims, 7 Drawing Sheets

CURING CHARACTERISTICS MEASURING APPARATUS AND MEASURING METHOD

This application is based on Japanese Patent Application No. 11-30648 (1999) filed Feb. 8, 1999, the content of which is incorporated hereinto by reference.

BACKGROUND OF THE INVENTION

1. Field of the Invention

The present invention relates to a curing characteristics measuring apparatus which is capable of measuring curing behaviors of a thermosetting resin or a composite material containing the same and to a curing characteristics measuring method.

2. Description of the Related Art

To know whether or not a thermosetting resin or a composite material containing the same has predetermined characteristics after curing, or, whether or not curing thereof begins and completes in a predetermined time under a specific temperature or pressure, a curing characteristics test is performed. For this purpose, a test has heretofore been conducted by partly changing the shape of a die of a viscoelasticity tester for measuring vulcanization characteristics of rubber (hereinafter referred to as "vulcanization tester").

Vulcanization testers for rubber are described in ISO3417, ISO6502, JIS K6300 and the like. Further, testers having a die devised for curing characteristics test of themosetting resins are described in Japanese Patent Application Publication No. 7-72710 (1995), Japanese Utility Model Application Publication No. 5-2841 (1993) and the like. The above-described vulcanization tester is an apparatus in which an unvulcanized rubber sample is charged in a sample chamber having a fixed surface and a rotation-vibrating drive surface, a torsional vibration is applied to the sample through the drive surface to record the changes as a curve while measuring a shearing stress generated in the sample as a vibration torque through the fixed surface or the drive surface. Still further, the die devised for curing characteristics test of thermosetting resins has devised grooves provided on the surface to prevent slipping between the die surface and the sample.

A thermosetting resin or a composite material containing the same is large in degree of volume contraction associated with curing reaction as compared to vulcanization reaction rate of rubber. Hereinafter this phenomenon is referred to as "curing shrinkage". In the prior art curing characteristics test apparatus, even if provided with the above-described slipping prevention grooves, when the curing shrinkage is considerable, in the curing process of the sample, a gap is generated between the inner wall of the sample chamber and the sample, resulting in such problems that a torsional vibration provided from the drive surface is not effectively transmitted to the sample, and/or a shearing stress generated in the sample is substantially damped before it is transmitted completely to a torque detection mechanism. Therefore, with such a test apparatus, there is no reproducibility of data and only part of necessary characteristics can be measured.

Group (A) of curves in FIG. 1 shows a practical example of such unsatisfactory test results. These are examples measured by repeated measurements by a prior art test apparatus of a sample which causes volume contraction during curing reaction. The test apparatus used is equipped with a die devised for curing characteristics test of thermosetting resin, which is described, for example, in Japanese Patent Application Publication No. 7-72710 (1995), Japanese Utility Model Application Publication No. 5-2841 (1993).

A prior art apparatus and measuring method will be described using a practical example. Construction of a measuring apparatus which presently is widely used is exemplified in FIG. 2. By rotation-vibration of a drive shaft 8, a torsional vibration is applied to a sample charged in a sample chamber 26 through a drive die 2 directly linked to the shaft 8, and a shearing stress generated inside the sample is transmitted in the form of a vibration torque to a torque detection die 1. Since the torque detection die 1 is supported by a torque detection mechanism 14 through a torque detection shaft 7, the vibration torque and a temporal change thereof are recorded by electrical means or the like through the torque detection mechanism 14.

The sample chamber 26, in addition to the torque detection die 1 and a drive die 2, comprises a torque detection side fixed die 3, and a drive side fixed die 4. Of these, the upper part from the torque detection die 1 and the torque detection side fixed die 3 is movable in upward and downward direction in the figure by an air cylinder 23 when loading/unloading the sample. On the other hand, since the drive die 2 and the drive side fixed die 4 are fixed with respect to the vertical direction in FIG. 2, the sample charged in the sample chamber 26 is maintained in a sealed state during measurement by a tightening pressure of the air cylinder 23. All the components constituting the sample chamber 26 are maintained at a predetermined measurement temperature by means of appropriate heater/temperature controllers 19, 20, 21 and 22. Numeral 5 indicates an upper seal, 6 is a lower seal, 10 is a motor, 11 is an eccentric rotary shaft, 12 is a crank arm, 13 is a torque arm, 15 and 16 are heaters, 17 is an upper base supporting an upper measuring part B and the like comprising the upper die 1 and the upper fixed die 3 and the like, 18 is a lower base supporting a lower measuring part A and the like comprising the lower die 2 and the lower fixed die 4 and the like, and 24 is a flash collector. Detailed construction in the vicinity of the sample chamber 26 is shown in FIGS. 3 and 4. Description of the respective figures will be made along with description of the measurement examples described below.

In FIG. 3, numeral 66 indicates a sample, 66A is a sample overflowed into the flash collector. In FIG. 4, numeral 64A indicates a cutout part of a seal plate support plate 64, 65A is a collar part of a seal plate 65, and 69 is a spot facing hole for a fixing screw.

The sample 66 used in the measurement example in FIG. 1 is an unsaturated polyester type thermosetting resin. This sample 66 is a viscous liquid having a fluidity at room temperature, and its volume contraction associated with curing is as large as about 7%. This value is one of the largest values among themosetting resins. The sample 66 is injected into the sample chamber 26 in FIG. 2. FIG. 3 shows an enlarged diagram of the sample chamber 26. The shape of a torque detection die (upper die) 61 shown in FIG. 3 is conical form, different from the example in FIG. 2, however, there is no substantial difference even if it is in a disk form. In addition, in the description hereinafter, for simplicity, the torque detection die 61 is referred to as an upper die, a torque detection side fixed die 63 as an upper fixed die, a drive die 62 as a lower die, and the seal plate support plate 64 as a lower fixed die.

FIG. 4 shows an exploded perspective diagram of components constituting the sample chamber 26. The seal plate 65 and the seal plate support plate 64 combinedly function as the lower fixed die, however, for convenience of removing cured sample and cleaning after the completion of measurement, the seal plate support plate 64 and the seal plate 65 have a separable structure.

After injecting the sample 66, the sample chamber 26 is rapidly closed, and driving of the lower die 62 shown in FIG. 3 is started. The driving is performed in sinusoidal rotation-vibration of an amplitude angle of ±¼ degree at a frequency of 1.6 Hz about the drive shaft 8 shown in FIG. 3. This rotation-vibration is transmitted to the sample 66 to generate a shearing stress according to its viscoelasticity inside the sample, which is transmitted as a vibration torque to the torque detection shaft 7 through the upper die 61 shown in FIG. 3. The vibration torque is detected by the torque detection mechanism, which is directly connected, and the state of temporal changes thereof is recorded as a curve. Normally, in this curve, only amplitudes of torque sinusoidal wave are recorded.

Temperatures of the five parts constituting the above sample chamber, namely, the upper die 61 shown in FIG. 3, the lower die 62, the upper fixed die 63, the seal plate 65, and the seal plate support plate 64 are controlled by the heaters 16, 20, 21, and 22 shown in FIG. 2 and temperature controllers (not shown), and maintained at a predetermined temperature (130° C. in the present example). As a result, temperature of the sample 66 maintained at room temperature begins to increase at the same time it is injected into the sample chamber, and rapidly reaches a predetermined curing temperature.

At the same time the air cylinder 23 is moved down to close the sample chamber 26, driving of the lower die 62 is started, and the vibration torque is detected. A record of temporal changes of the detected torque amplitude is the group (A) of curves shown in FIG. 1, which is referred to as a curing behavior curve or a curing curve. The group (A) of curves shows repeatedly measured results of the same sample under the same conditions. Group (B) of curves will be described later. The axis of abscissas of FIG. 1 indicates the passage of time (min) from sample charge, and the axis of ordinates indicates amplitude values of vibration torque corresponding to each time passage. The injected sample 66 from an initial flexible and fluid state rapidly begins to cure after a certain time lapse, and while decreasing curing rate with the progress of curing, reaches a hard saturation state in due course of time. The state of this series of thermal curing process can be seen from the group (A) of curves in FIG. 1. The time at which rapid curing begins is referred to as a curing start time, and a curing reaction rate can be determined from gradient of the curve after curing start and changes thereof. The two factors of the curing start time and the curing reaction rate are respectively important industrial indices characterizing the rate of reaction at that temperature of the resin sample, which is largely varied with the curing temperature. Further, a torque of the part in which the curing curve of the latter half is almost flat (hereinafter referred to as an after-cure torque) is a measure of hardness of the cured resin at that temperature, which is normally soft as the measuring temperature increases, that is, it has a heat softening type temperature dependence. Therefore, to know these three factors and the relationship between these factors and temperature quantitatively means to obtain an important guideline for quality control and process design of the resin composition, and in performing material design of compositional formulation and construction of the composite material itself.

In practice, however, as shown in the curve group (A) of FIG. 1, it is often that the curing curve in the latter half of curing process is disturbed and repeatability is not obtained. This is a phenomenon which is conspicuous when curing shrinkage is large. A cause therefor is considered as due to the fact that pressing force important for slip prevention in the interface between the sample and the upper and lower dies is decreased with the progress of the reaction, depending on the magnitude of shrinkage, resulting in a gap on the interface, the vibration torque is largely damped during the time when it is transmitted in the course of the drive die→ sample→ torque detection die. In such a case, among the above three factors, although some quantitativity is obtained as to the curing start time, quite no quantitativity is obtained for the remnant two factors.

As described above, when curing behaviors of thermosetting resins are measured by the prior art curing characteristics measuring apparatus, there have frequently occurred problems in that a gap is generated between the sample and the sample chamber in association with curing shrinkage characteristic of thermosetting resins, therefore, torsional vibration provided from the drive surface is not effectively transmitted, and/or shearing stress generated in the sample is substantially and randomly damped before it is completely transmitted to the torque detection mechanism, resulting in incapability of exact measurement.

SUMMARY OF THE INVENTION

It is therefore an object of the present invention to provide a curing characteristics measuring apparatus and measuring method which solves such prior art problems and is capable of exactly and efficiently measuring the curing curve.

In accordance with the present invention which attains the above object, there is provided a curing characteristics measuring apparatus characterized in that a separable sample chamber having a fixed surface and a rotation-vibrating drive surface is charged with a sample having a viscoelasticity, a torsional vibration is applied to the sample through the drive surface, and a shearing stress generated in the sample is measured as a torque through the fixed surface or part thereof, wherein means is provided for changing volume of the sample chamber following volume change generated in curing process of the sample.

The means for changing volume of the sample chamber comprises a structure wherein at least one of the drive surface and the fixed surface is movable in a direction of changing an interfacial distance between both surfaces, a means for achieving the movement following volume change generated in curing process of the sample.

The drive surface is a sample contact surface of a drive die, the fixed surface is a sample contact surface of a torque detection die, a torque detection side fixed die and a seal plate, and the movable structure is provided with a spring function capable of deflecting in a direction of changing an interfacial distance between the drive surface and the fixed surface.

The means for achieving the movement uses air pressure as a drive source. A value of the air pressure is possible to be varied according to a change in shearing stress in curing process of the sample.

A curing characteristics measuring method of the present invention characterized in that a separable sample chamber having a fixed surface and a rotation-vibrating drive surface is charged with a sample having a viscoelasticity, a torsional vibration is applied to the sample through the drive surface, and a shearing stress generated in the sample is measured as a torque through the fixed surface or part thereof, wherein a measurement is performed while changing volume of the sample chamber following volume change generated in curing process of the sample.

The measurement is performed while changing volume of the sample chamber by moving at least one of the drive surface and the fixed surface in a direction to change interfacial distance between both surfaces.

The sample is contacted with a rotation-drive surface of a drive die, surfaces contacting with the sample of the torque detection die, the torque detection side fixed die and the seal plate are fixed with respect to rotational direction of drive die, and a support body for supporting the seal plate is provided with a spring function capable of deflecting in a direction of changing an interfacial distance between the drive surface and the fixed surface, thereby reducing volume of the sample chamber in accordance with a volume contraction generated in curing process of the sample.

The movement is achieved using air pressure as a drive source.

A value of the air pressure is varied according to a change in shearing stress in curing process of the sample.

As described above, with the present invention, following the phenomenon that the thermosetting resin sample shrinks in the curing process, volume of the sample chamber comprising the drive surface of the drive die and the torque detection surface of the fixed die is reduced, and appropriate contact bonding conditions are always maintained between the sample and the drive surface and between the sample and the torque detection surface, thereby preventing slip on the interface thereof and efficiently detecting and recording exact curing curves over the entire curing process of the sample.

The above and other objects, effects, features, and advantages of the present invention will become more apparent from the following description of embodiments thereof taken in conjunction with the accompanying drawings.

DETAILED DESCRIPTION OF PREFERRED EMBODIMENTS

In the present invention, when a sample chamber having a fixed surface and a rotation-vibrating drive surface of a curing characteristics measuring apparatus is charged with a sample having a viscoelasticity, the sample is applied with a torsional vibration through the drive surface, and a shearing stress generated in the sample is measured as a torque through the fixed surface or the drive surface, wherein the volume of the sample chamber is reduced according to a volume contraction generated in the curing process of the sample to measure curing characteristics of a thermosetting resin. With this configuration, a torque measurement error due to curing shrinkage in the curing reaction process of the resin is eliminated.

More specifically, the sample is contacted with the rotation-drive surface of the drive die, the torque detection die, the torque detection side fixed die, and the surface of the seal plate contacting with the sample are fixed with respect to the rotational direction of the drive die, and a seal plate support body for supporting the seal plate is provided with a spring function to deflect in a direction of changing an interfacial distance between the drive surface and the fixed surface, thereby reducing the volume of the sample chamber in accordance with a volume contraction generated in the curing process of the sample.

Embodiment

Figure 5:
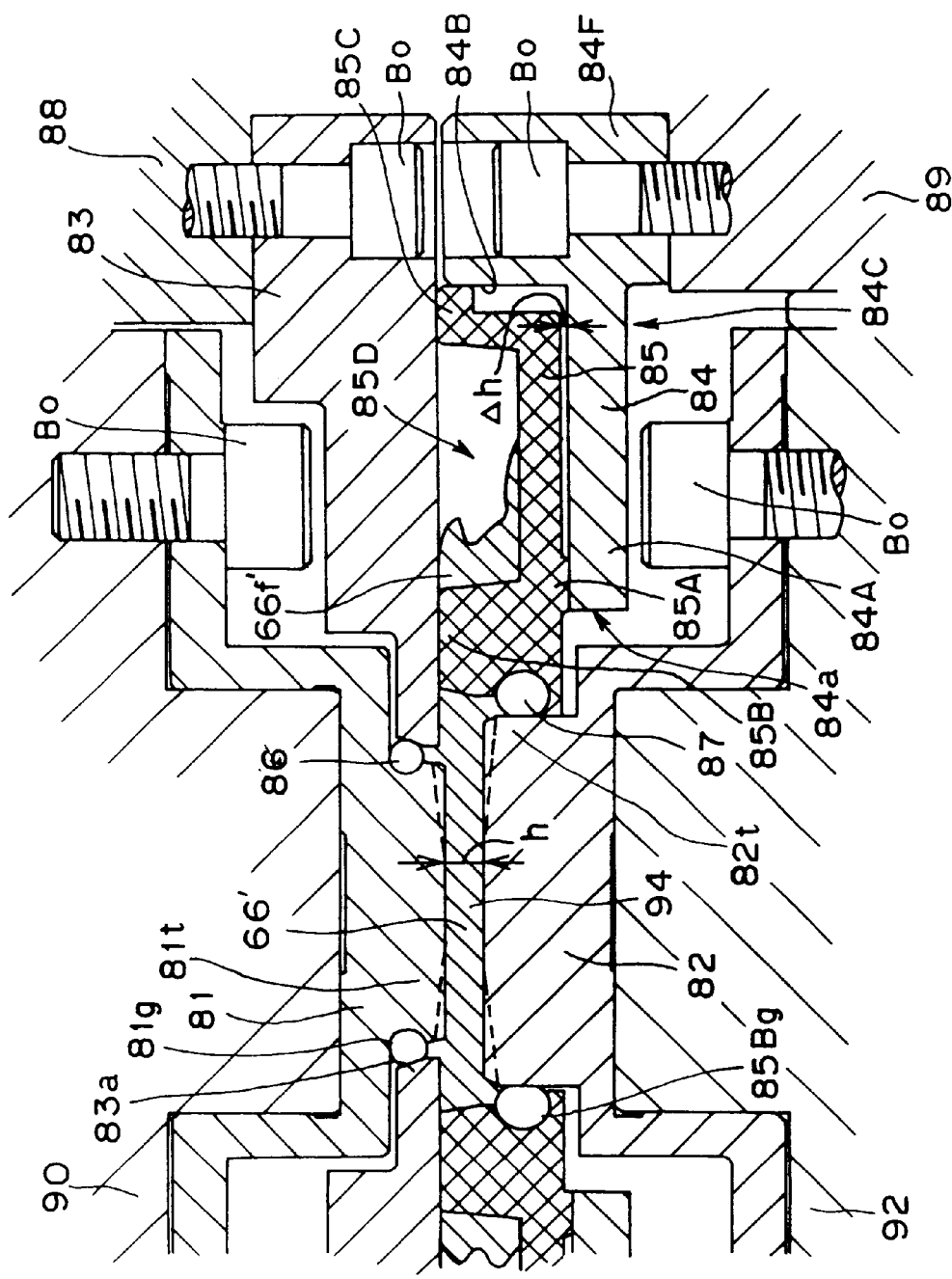
FIG. 5 is a sectional diagram in the vicinity of a sample chamber of an embodiment of curing characteristics measuring apparatus according to the present invention.

In the following, an embodiment of the present invention will be described in detail with reference to the drawings. FIG. 5 shows the vicinity of the sample chamber of an embodiment of the present invention.

Figure 2:
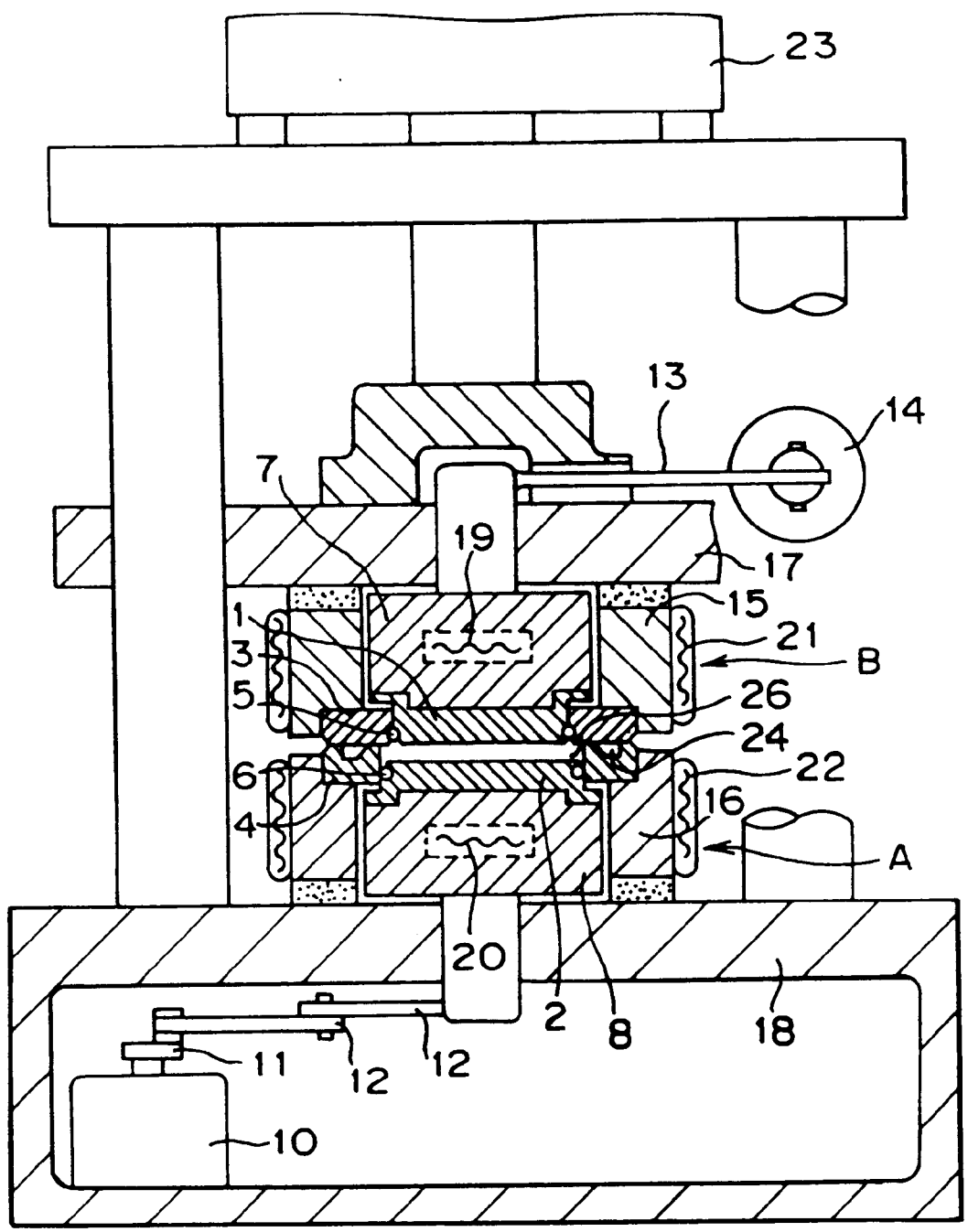
FIG. 2 is a sectional diagram of a prior art curing characteristics measuring apparatus.

The above-described drive system, torque measuring system, air cylinder and the like as described in the prior art are not shown, however, such drive system, torque measuring system, and air cylinder have the same structures as known structures, for example, as shown in FIG. 2.

In FIG. 5, numeral 81 indicates an upper die, 82 is a lower die, and 83 is an upper fixed die, which respectively correspond to the upper die 61, the lower die 62 and the upper fixed die 63 in the prior art apparatus. The upper fixed die 83, in its outer peripheral part, is fastened onto a hot platen 88 with bolts Bo. FIG. 5 shows a state where the upper fixed die 83 is in a position close to a seal plate support plate 84 which will be described later.

Numeral 84 indicates the seal plate support plate, and 85 is a seal plate. Numeral 86 is an O-ring attached to a groove 81g provided at a base end part of a part under transmittal 81t provided with a plurality of radial grooves formed on the upper die 81. 87 is an O-ring attached to a groove 85Bg provided on an inner peripheral part of an upper surface projection part 85B of the seal plate 85 which will be described later.

The upper die 81 is fastened with the bolt Bo to an end part of the torque detection shaft 90 disposed opposite to the upper fixed die 83. The part under transmittal 81t of the upper die 81 is rotatably engaged with an inner peripheral part 83a of the upper fixed die 83 through the O-ring 86. The torque detection shaft 90 is fixed to a base member which is selectively moved up/down by an air cylinder (not shown).

Figure 3:
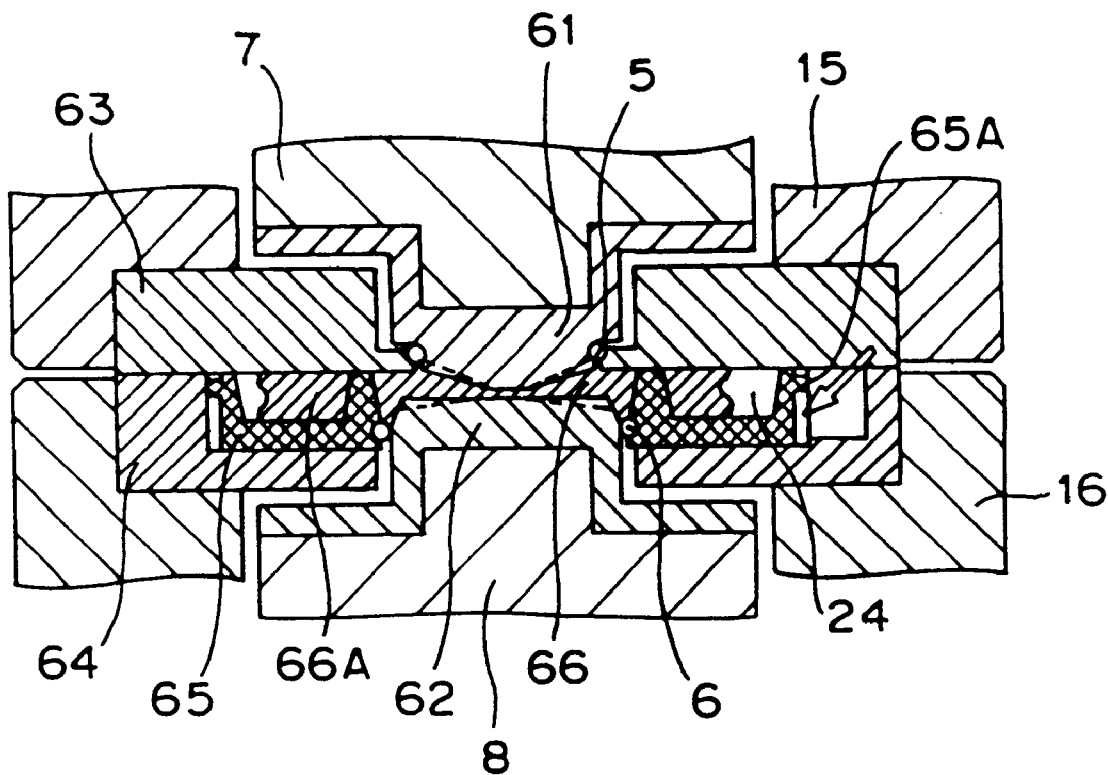
FIG. 3 is a diagram showing details in the vicinity of a sample chamber of the prior art apparatus.
Figure 4:
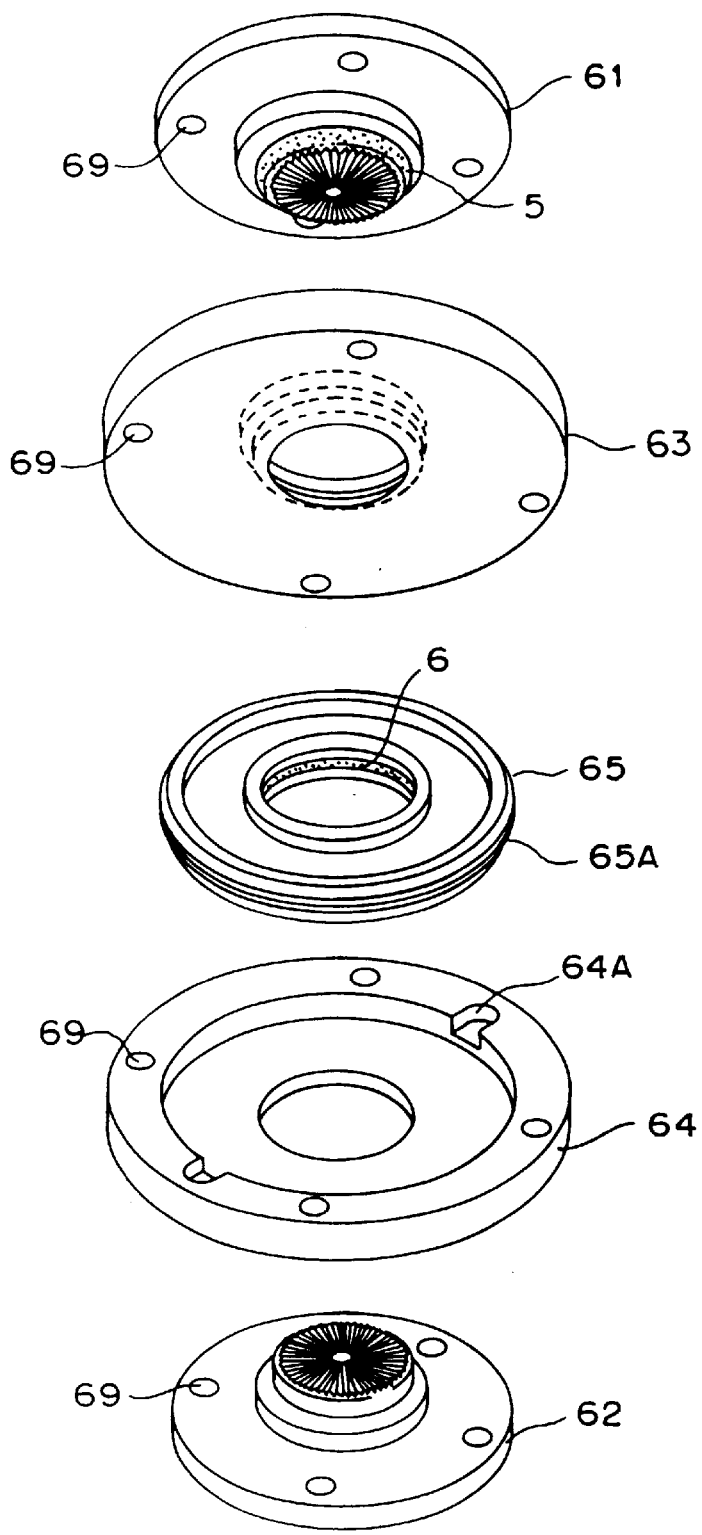
FIG. 4 is an exploded perspective diagram of respective parts constituting the sample chamber of the prior art apparatus.

The present invention is characterized in that part of the seal plate support plate 84, which is a component of the drive side fixed die, is provided with a coned disc spring structure. That is, shapes of the seal plate support plate 64 and the seal plate 65 in the prior art viscoelasticity measuring apparatus shown in FIGS. 3 and 4 are changed to as follows.

Figure 6:
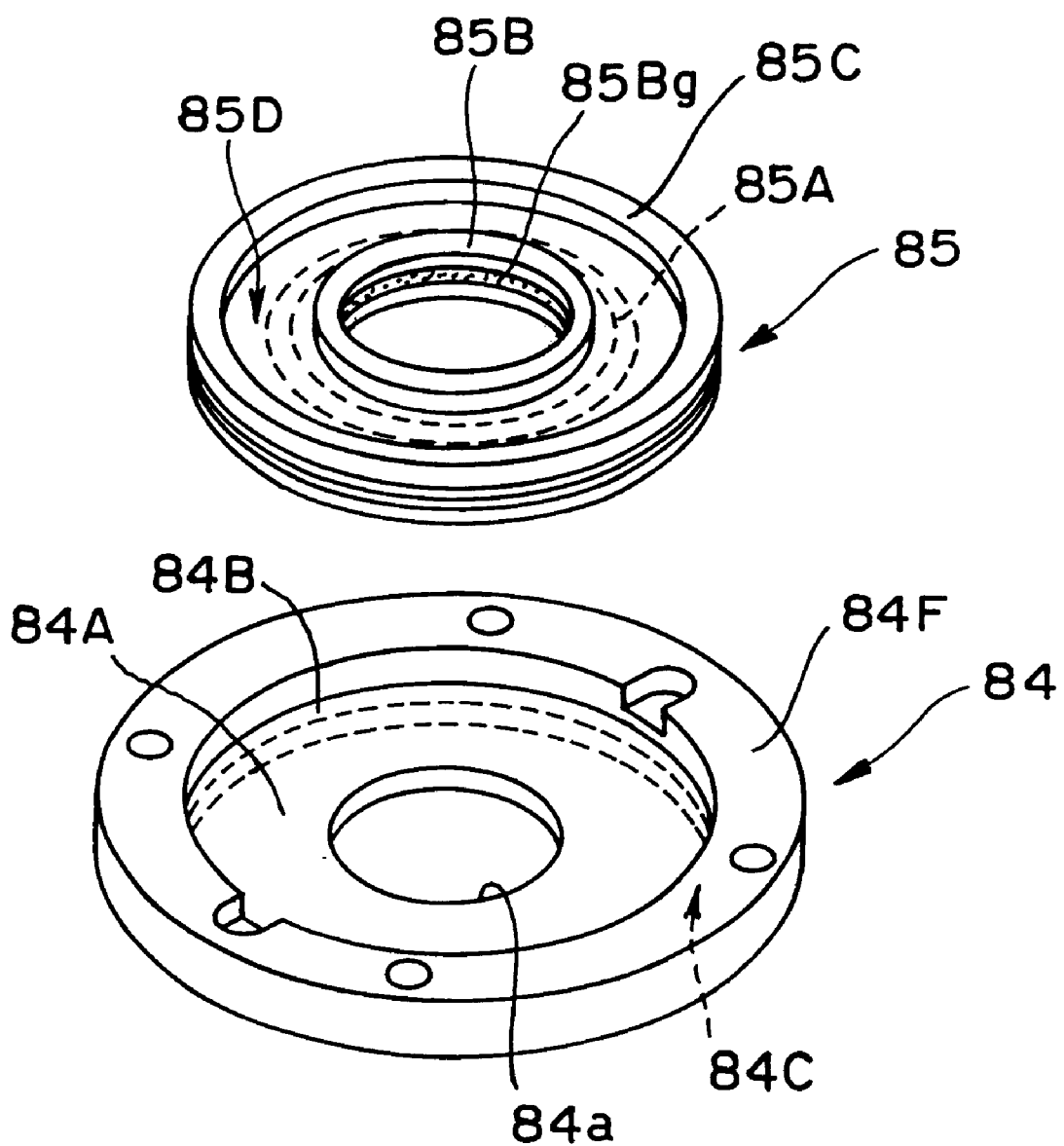
FIG. 6 is a perspective diagram showing an outer appearance of a seal plate and a seal plate support plate used in an embodiment of curing characteristics measuring apparatus according to the present invention.

The ring-formed seal plate 85 is made of, for example, a carbon steel material, and, as shown in FIGS. 5 and 6, has an upper surface projection part 85B formed as an inner ring and an outer ring part 85C formed on the periphery of the upper surface projection part 85B. Between the upper surface projection part 85B and the outer ring part 85C, when assembled, an annular recess 85D is formed as a flash well opening towards the upper fixed die 83.

At the part closer to the inner periphery of the lower surface of the upper surface projection part 85B disposed opposite to the disk-formed part 84A of the seal plate support plate 84 which will be described later, a ring-formed lower surface projection part 85A as shown in the figure is provided at a predetermined height.

An upper surface of the upper surface projection part 85B and an upper surface of the outer ring part 85C are on a same plane, and, as shown in FIG. 5, when the position of the upper fixed die 83 is close to the seal plate support plate 84, the upper surface of the upper surface projection part 85B and the outer ring part 85C simultaneously contact against lower surface of the upper fixed die 83, respectively.

Therefore, the seal plate 85, when mounted to the seal plate support plate 84, is supported by contacting against the disk-formed part 84A of the seal plate support plate 84 by only this part (85A) against a pressure from the upper fixed die 83, and the seal plate 85 is shaped so that a spacing Δh is remained between the other part of the lower surface and the disk-formed part 84A.

Further, inside the upper surface projection part 85B, a transmission part 82t of the lower die 82 through the O-ring 87 is rotatably engaged through an opening part 84a of the seal plate support plate 84. The lower die 82 is linked to the drive shaft 92 with the bolt Bo.

The O-rings 86 and 87 are seals for preventing leakage of the sample 66' from the sample chamber 94 which will be described later, and referred respectively to as an upper seal and a lower seal and are normally used as a combination of a fluororubber-made O-ring (O-ring 86) with a fluoroplastic-made O-ring (O-ring 87), however, during downward movement of the seal plate 85, a frictional resistance existing between the lower seal 87 and the lower die 82 is not preferable because it acts in a direction to reduce contact bonding force of the sample surface. However, since, in addition to the fact that the material of the lower seal is fluoroplastic in with a small frictional coefficient, and fortunately the both parts are forcedly and always subjected to relative swinging in the peripheral direction during measurement, resistance to the relative movement in the vertical direction is extremely small and are in a relation easy to achieve smooth relative vertical movement according to a change in pressing force, the above-described effect to reduce the contact bonding force is nearly negligible.

On the other hand, the ring-formed seal plate support plate 84 comprises a disk-formed part 84A made of, for example, a spring carbon steel material and having an opening 84a nearly at the center and a flange part 84F formed in a ring connecting to the entire outer peripheral part of the disk-formed part 84A. The thickness of the disk-formed part 84A is set to deflect by a predetermined amount when applied with a predetermined load. At the part surrounded by an upper surface of the disk-formed part 84A and the inner peripheral surface of the flange part 84F, a recess 84B engaged with the seal plate 85 is formed. Depth of the recess 84B is set to a predetermined size which is slightly smaller than the circumference thickness of the seal plate 85 so that the downward deflection of disk-formed part 84A is not interfered. Further, at the part surrounded by the other end surface of the disk-formed part 84A and the inner peripheral surface of the flange part 84F, a recess 84C having a depth such that sufficient spacing leaves between a head of the lower boltBo (a depth of the recess 84C is smaller than that of the recess 84B as shown FIG. 5) is formed. This enables the inner peripheral portion of the disk-formed part 84A to deflect downwardly relative to the flange part 84F as the supporting point when a press down force is applied at the upper surface as the point of application of the force in a direction along its center axis line. As a result, the seal plate support plate 84 functions as a so-called coned disc spring (above-mentioned disk-formed part 84A is also referred to as a coned disc spring part 84A, hereinafter).

The flange part 84F is provided with a plurality of holes for penetrating bolts Bo. The flange part 84F is connected to the hot platen 89 by driving the respective bolts Bo through the holes to the screw holes of the hot platen 89.

Therefore, when the position of the upper fixed die 83 is close to the seal plate support plate 84, the sample chamber 94 injected with the sample 66' is surrounded by the upper fixed die 83, the part under transmittal 81t of the upper die 81, the inner peripheral surface of the upper surface projection part 85B of the seal plate 85, the transmission part 82t of the lower die 82, and the O-rings 86 and 87 to form a sealed state.

In the above sealed state, when the pressing force of the air cylinder to the upper fixed die 83 is increased according to increase of a working air pressure from initial pressure as follows, for balancing with the increased pressing force, the coned disc spring part 84A of the seal plate support plate 84 is deflected downward, the seal plate 85 is moved down along with the lower surface projection part 85A, and all members (upper fixed die 83, O-ring 86, upper die 81) supported on the seal plate 85 are integrally moved downward.

If the amount of thickness decrease corresponding to volume contraction of the sample 66' is smaller than the amount of movement, since the vertical position of the lower surface of the sample 66' is fixed by the lower die 82, a greater part of increase of the pressing force is supported by the sample 66', and the surface of the upper die 81 and the surface of the upper fixed die 83 move down following the shrinking sample 66', and therefore, the significant decrease or extinction of contact bonding force of the upper and lower dies (81, 82) to the surface of the sample 66' is prevented.

The above is description of the mechanism in which the volume of the sample chamber 94 is reduced following curing shrinkage of the sample 66' to maintain a contact bonding force important for preventing slip in the interface of the sample 6' and the die.

The spacing Δh between the seal plate 85 and the seal plate support plate 84 is, as described above, a space for deflection of the coned disc spring part (disk-formed part 84A), and, at the same time, doubles also as a deflection stopper for preventing fracture of the coned disc spring part even when it is applied with an excessive pressing force exceeding its elastic limit and preventing occurrence of excessive instability of distance between dies (shown as h in FIG. 5) which is important as an instrumental constant of torque generation due to unlimited deflection.

Figure 7:
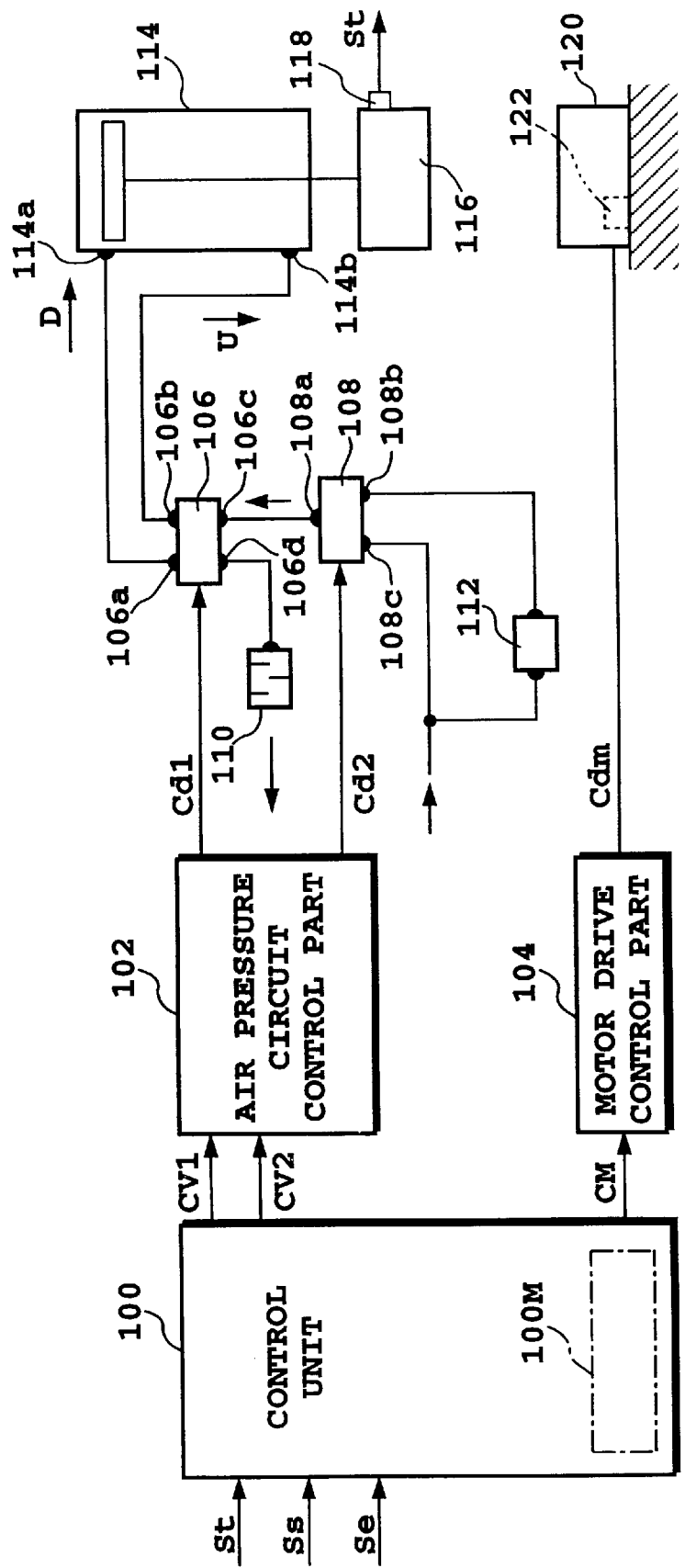
FIG. 7 is a schematic diagram showing the construction of a control unit with an air pressure circuit provided in an embodiment of curing characteristics measuring apparatus according to the present invention.

Further, an example of curing characteristics measuring apparatus according to the present invention is, as shown in FIG. 7, provided with a control unit 100 for controlling an air pressure circuit part for supplying working air to an air cylinder 114.

The control unit 100 has a memory part 100M for storing respective operation control program data, reference torque amplitude data described later according to the respective samples 66' and the like.

The control unit 100 is applied with an instruction signal Ss representing test start instruction, an instruction signal Se representing test end instruction, and a detection output signal St from a load cell 118 for detecting a torque transmitted to the torque detection shaft 90.

As schematically shown in FIG. 7, an air cylinder 114 having a rod connected to a movable side measuring unit 116 comprising a base supporting the torque detection shaft 90, the hot platen 88, the upper fixed die 83 and the like is disposed at a position above the movable measuring unit 116 to be vertically moved relative to a fixed side measuring unit 120 disposed opposing the movable side measuring unit 116 which is disposed beneath. Further, the fixed side measuring unit 120 comprises the hot platen 89, the drive shaft 92, a motor 122 for rotating the drive shaft 92 through a belt and the like.

Ports 114a and 114b of the air cylinder 114 are respectively connected with ports 106a and 106b of a 4-port solenoid valve 106. Still further, the port 106c of the 4-port solenoid valve 106 is connected with a port 108a of a 3-port solenoid valve 108, and a port 106d of the 4-port solenoid valve 106 is connected with a silencer 110.

A port 108c of the 3-port solenoid valve 108 is connected with an air supply source (not shown). Further, a supply passage with one end connected to the air pressure supply source and the other end connected to a port 108b of the 3-port solenoid valve 108 is provided with a pressure reducing valve 112. Pressure of working air of the air pressure supply source is set to, for example, 0.5 (MPa). Still further, the pressure reducing valve 112 is set to reduce air pressure from the air pressure supply source to, for example, 0.1 (MPa).

The 4-port solenoid valve 106 and the 3-port solenoid valve 108 are respectively controlled according to drive control signals from an air pressure circuit control part 102.

A control unit 100 forms control signals CV1 and CV2 and supplies them to the air pressure circuit control part 102 so that after the predetermined sample 66' having a volume slightly greater than the volume of the sample chamber 94 is previously injected inside the upper surface projection part 85B, the movable side measuring unit 116 is moved down according to the instruction signal Ss to contact the upper fixed die 83 against the seal plate 85 at a predetermined initial pressure (P1). The air pressure circuit control part 102, according to the control signals CV1 and CV2, and forms drive control signals Cd1 and Cd2 so that the port 108b of the 3-port solenoid valve 108 is communicated with the port 108a and the port 106c of the 4-port solenoid valve 106 is communicated with the port 106a, the port 106b is communicated with the port 106d, and supplies the respective signals to the 4-port solenoid valve 106 and the 3-port solenoid valve 108.

Therefore, working air is supplied to a port 114a of the air cylinder 114 along the direction shown by arrow D, and air therein is discharged through a port 114b.

That is, after injecting the sample, both members of the upper die 81 and the upper fixed die 83 are pressed downward integrally under an initial pressure (P1) by the air cylinder 114 to fill the inside of the sample chamber 94 with the sample 66'. At this moment, excess sample 66f is flowed out through a contact surface (a so-called pinch-off surface) of the ring-formed projection part 85B close to the upper surface and inner periphery of the seal plate 85 and the upper fixed die 83 to an outside recess 85D (flash well).

At this time, the control unit 100 forms a control signal CM so as to make the motor 122 operative, and supplies it to a motor drive control part 104. The motor drive control part 104 forms a drive control signal Cdm on the basis of the control signal CM, and supplies it to the motor 122. This rotates the transmission part 82t of the lower die 82 in a predetermined rotational direction, and rotates the part under transmittal 81t of the upper die 81 following through the sample 66' in the sample chamber 94. The load cell 118 always outputs the detection output signal St according to the rotation of the torque detection shaft 90.

Next, the control unit 100 refers to a reference torque amplitude value data which is previously read and set from the memory part 100M, for example, according to the detection output signal St, when the torque amplitude value represented by the detection output signal St exceeds the reference torque amplitude value, it is judged to be a transition point where the transmission torque sharply rises with a change of hardness of the sample 66'. In other words, the transition point as a change in a shearing stress generated in the sample 66' can also be said to be a point of time at which curing of the sample 66' begins with the passage of time, reduction of fluidity and increase of torque amplitude simultaneously progress, and detected torque value exceeds a previously set threshold value.

At this time, the control unit 100 forms the control signal CV2 so as to contact the upper fixed die 83 against the seal plate 85 at an increased predetermined pressure (P2) and supplies it to the air pressure circuit control part 102. Ratio of the pressure (P2) to the initial pressure (P1) is, for example, practically about 1.5 to 10 times.

The air pressure circuit control part 102 forms a drive control signal Cd2 on the basis of the control signal CV2 so as to communicate the port 108c of the 3-port solenoid valve 108 with the port 108a and supplies it to the 3-port solenoid valve 108.

This supplies pressure-increased working air supplied through the port 108c to the port 114a of the air cylinder 114 along the direction shown by arrow D. Accordingly, the pressing down force of the movable side measuring unit 116 is increased by a buildup of air pressure of the air cylinder 114 to distribute a portion of the pressing down force to an outer element as follows.

Therefore, pressing force of the upper fixed die 83 to the seal plate 85 is increased.

Next, the control unit 100 stops supplying the control signal CM to the motor drive control part 104 on the basis of instruction signal Se representing test end instruction. Further, the control unit 100 forms control signals CV1 and CV2 so as to separate the movable side measuring unit 116 relative to the fixed side measuring unit 120, and supplies them to the air pressure circuit control part 102. The air pressure circuit control part 102 forms drive control signals Cd1 and Cd2 so as to cause the port 108b of the 3-port solenoid valve 108 to communicate with the port 108a according to the control signals CV1 and CV2, the port 106c of the 4-port solenoid valve 106 to communicate with the port 106b, and the port 106a to communicate with the port 106d, and supplies them to the 4-port solenoid valve 106 and the 3-port solenoid valve 108, respectively.

Therefore, working air is supplied to the port 114b of the air cylinder 114 along the direction shown by arrow U, and inside air is discharged through the port 114a. Therefore, the movable side measuring unit 116 is returned to the initial position.

When it is necessary to control increasing rate of the pressing force appropriately, a throttle valve may be included halfway in the compressed air flow passage, or pressure increasing compressed air sources be provided in multiple stages, rather than two stages, which are changed over successively, or an automatic pressure control valve having a function to change secondary pressure continuously be used to other pressure increasing methods increase the pressure continuously according to an increase of torque.

The above increase amount of pressing force is distributed to an inside element (upper die 81, sample, lower die 82) and an outside element (upper fixed die 83, seal plate 85, seal plate support plate 84) as mechanical parallel elements.

Pressing force increase amount distributed to the outside element is a prime mover of the mechanism in which the volume of the sample chamber is reduced following curing shrinkage of the sample.

The distribution ratio is such that a greater part is distributed to one of higher rigidity according to the ratio of inside and outside vertical rigidities because these elements are parallel elements. Therefore, to maintain a sufficient contact bonding state between the sample 66' as an inside element and the interface of the upper and lower dies during a measurement, it is necessary to set the vertical direction rigidity of the outside element to a slightly lower value compared to that of the inside element.

There is a fear that a flexibility of the sample 66' itself located at the center of the inside element decreases vertical direction rigidity of the entire inside element.

However, the modulus governing factor governing the vertical direction rigidity is not lateral direction modulus (G) or Young's modulus (E) which are general-purpose measures of flexibility but volume elastic modulus (B) in this case.

In general, since volume elastic modulus (B) of a resin is very high almost irrespective of magnitude of its shearing modulus, and is not substantially changed between before and after the curing, vertical direction rigidity of the inside element is sufficiently large. Therefore, if flow out of the sample to the recess part 85D (flash well) is not added after pressure increase, it is relatively easy to design thickness and effective length in the radial direction of the coned disc part and provide an appropriate flexibility so that vertical direction rigidity of the outside element is smaller than that of the inside element. Therefore, the above fear is not necessary.

Further, setting the pressure increase timing to after reduction of fluidity is to prevent the above additional flow out.

Figure 1:
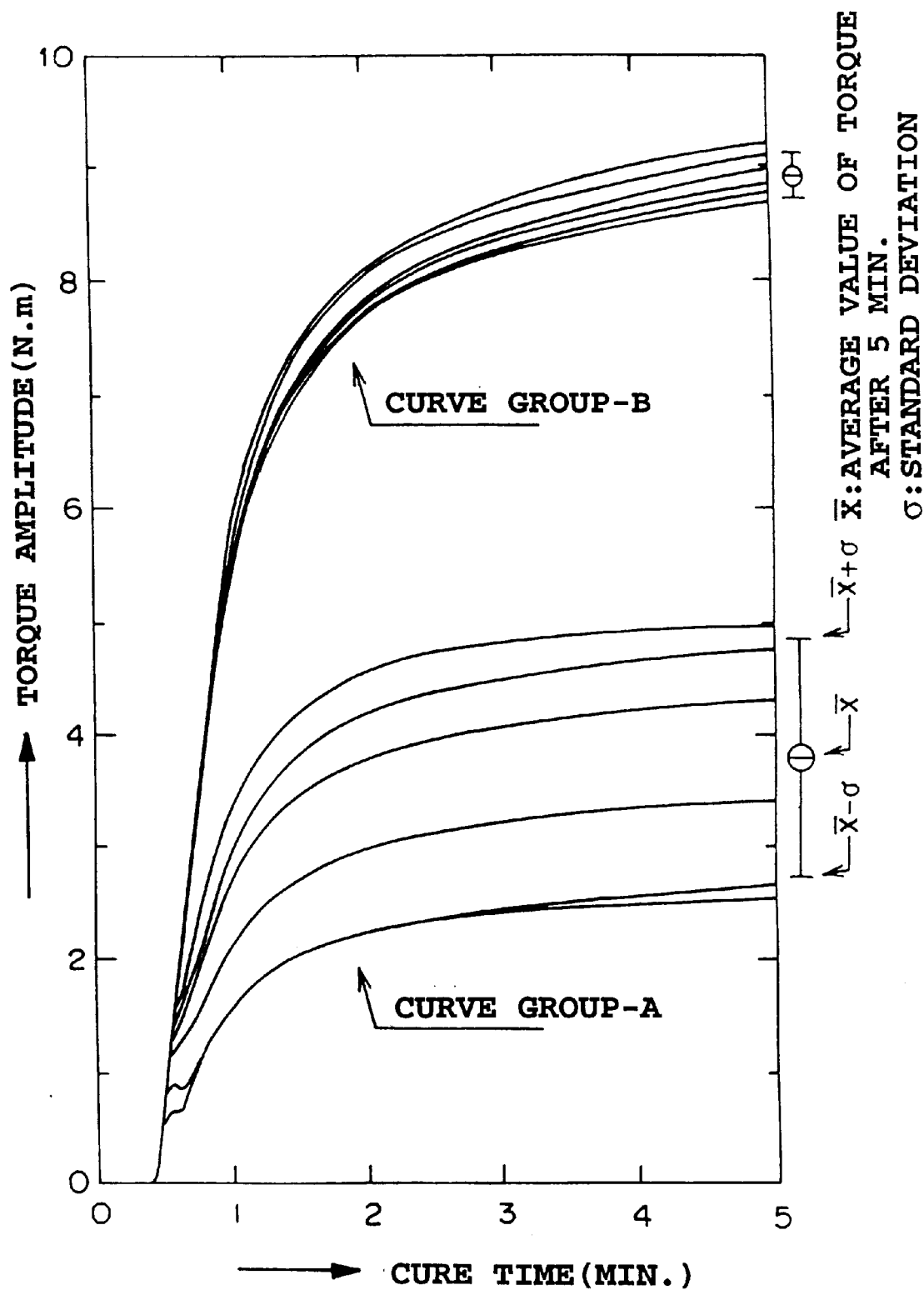
FIG. 1 is a characteristic diagram showing the relationship between curing time and torque amplitude.

The above increase in torque amplitude is a revelation of elasticity of the sample 66'. This means loss of its elasticity. In general, even when the pressing force is changed over so that the pressing force is large at a relatively low torque value in the initial stage of curing, new flow out from the sample chamber 94 to the recess part 85D can be effectively prevented. For example, the resin used in experimental example represented by the group (B) of curves in FIG. 1 is relatively low in viscosity before curing at the measuring temperature and relatively high in fluidity, however, it is confirmed that even when the pressure is changed over at a low torque value (0.1N·m) corresponding to about less than $\frac{1}{100}$ of the torque value after curing, additional flow out after pressure increase is prevented.

Further, a devise for improving removal of bubble is useful for obtaining a stable curing curve since when a bubble is remained inside at the time the sample chamber 94 is closed, the volume rigidity of the sample 66' is decreased according to the amount of the bubble.

Pressing force increase amount distributed to the outside element is transmitted through the upper fixed die 83→ upper surface projection part 85B of the seal plate → the lower surface projection part 85A→ inner peripheral part of the seal plate support plate 84. That is, deflection of the disk-formed part 84A (coned disc spring part) of the seal plate support plate 84 is increased even further. Therefore, even if the volume of the sample 66' is decreased during measurement, the lower surface projection part 85A of the seal plate 85 sinks downward following the shrinkage, and the O-ring 87 is moved downward while slipping according to the sinking distance thereof.

As a result, the upper die 81 and the lower die 82 come close to each other (h in FIG. 5 decreases), volume of the sample chamber 94 is decreased, and contact bonding state of the upper and lower die surfaces to the sample 66' is maintained, thereby preventing slip at above-mentioned the interface.

As described above, even with sample 66' which is liable to undergo curing shrinkage, the dies relatively move in a direction to narrow gap between the upper and lower dies following the shrinkage to decrease volume of the sample chamber, thereby achieving the structure of measuring part which is capable of maintaining contact bonding state necessary for preventing slip between the inner wall of the sample chamber 94 and the surface of the sample 66'.

Group (B) of curves in FIG. 1 shows repeated experimental example of curing curve measured by an example of curing characteristics measuring apparatus according to the present invention.

Sample and test conditions such as temperature, amplitude angle, sample chamber configuration and the like used in the experiment of the group (B) of curves are the same as the sample and test conditions of the curing curve group (A) according to the prior art system. That is, the sample 66' is an unsaturated polyester type thermosetting resin (curing shrinkage rate is about 7% in volume ratio), and measurement conditions are curing temperature 130° C., amplitude angle ±¼ degree, and frequency 1.6 Hz.

As can be seen from FIG. 1, the curve group (B) is considerably increased in torque after curing as compared with the curve group (A), the curve group (A) has a torque average value of 3.8 (N·m), whereas the curve group (B) has a torque average value after curing of 8.9 (N·m). Further, variation coefficient (standard deviation/average value: so-called CV value) of after-cure torque is remarkably as small as 2.3% as compared with 28% of the curve group (A). These significant differences show that while the curing torque in the prior art configuration is damped considerably and randomly following curing shrinkage of the sample 66', in the present invention, since contact bonding state is maintained during measurement, damping of torque is suppressed, and more stable curing curve can be measured. That is, the curve group (B) is the result showing reliability and good reproducibility of the system according to the present invention, showing a remarkable improvement compared with the prior art test apparatus. The present invention has been described on detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A curing characteristics measuring apparatus characterized in that a separable sample chamber having a fixed surface and a rotation-vibrating drive surface is charged with a sample having a viscoelasticity, a torsional vibration is applied to said sample through said drive surface, and a shearing stress generated in said sample is measured as a torque through said fixed surface or part thereof, wherein means is provided for reducing the volume of said sample chamber in response to shrinkage of said sample.

2. The curing characteristics measuring apparatus as claimed in claim 1, wherein said means for reducing volume of said sample chamber comprises a structure wherein at least one of said drive surface and said fixed surface is movable in a direction of changing an interfacial distance between both surfaces, a means for achieving said movement following volume change generated in curing said sample.

3. The curing characteristics measuring apparatus as claimed in claim 2, wherein said drive surface is a sample contact surface of a drive die, said fixed surface is a sample contact surface of a torque detection die, a torque detection side fixed die and a seal plate, and said movable structure is provided with a spring function capable of deflecting in a direction of changing the interfacial distance between said drive surface and said fixed surface.

4. A curing characteristics measuring apparatus, wherein a separable sample chamber having a fixed surface and a rotation-vibrating drive surface is charged with a sample having a viscoelasticity, a torsional vibration is applied to said sample through said drive surface, and a shearing stress generated in said sample is measured as a torque through said fixed surface or part thereof, and wherein means is provided for changing volume of said sample chamber following volume change generated in a curing process of said sample;

wherein said means for changing volume of said sample chamber comprises a structure wherein at least one of said drive surface and said fixed surface is movable in a direction of changing an interfacial distance between both surfaces, a means for achieving said movement following volume change generated in curing said sample;

said drive surface is a sample contact surface of a die drive, said fixed surface is a sample contact surface of a torque detection die, a torque detection side fixed die and a seal plate, and said movable structure is provided with a spring function capable of deflecting in a direction of changing an interfacial distance between said drive surface and said fixed surface; and said means for achieving said movement uses air pressure as a drive source.

5. A curing characteristics measuring apparatus characterized in that a separable sample chamber having a fixed surface and a rotation-vibrating drive surface is charged with a sample having a viscoelasticity, a torsional vibration is applied to said sample through said drive surface, and a shearing stress generated in said sample is measured as a torque through said fixed surface or part thereof, wherein means is provided for changing volume of said sample chamber following volume change generated in a curing process of said sample;

wherein said means for changing volume of said sample chamber comprises a structure wherein at least one of said drive surface and said fixed surface is movable in a direction of changing an interfacial distance between both surfaces, a means for achieving said movement following volume change generated in curing said sample;

said drive surface is a sample contact surface of a drive die, said fixed surface is a sample contact surface of a torque detection die, a torque detection side fixed die and a seal plate, and said movable structure is provided with a spring function capable of deflecting in a direction of changing an interfacial distance between said drive surface and said fixed surface;

said means for achieving said movement uses air pressure as a drive source; and value of said air pressure is possible to be varied according to a change in shearing stress in curing process of said sample.

6. A curing characteristics measuring method characterized in that a separable sample chamber having a fixed surface and a rotation-vibrating drive surface is charged with a sample having viscoelasticity, a torsional vibration is applied to said sample through said drive surface, and a shearing stress generated in said sample is measured as a torque through said fixed surface or part thereof, wherein a measurement is performed while reducing the volume of said sample chamber in response to shrinkage of said sample.

7. The curing characteristics measuring method as claimed in claim 6, wherein said measurement is performed while changing the volume of said sample chamber by moving at least one of said drive surface and said fixed surface in a direction to change interfacial distance between both surfaces.

8. The curing characteristics measuring method as claimed in claim 7, wherein said sample is contacted with a rotation-drive surface of a drive die, surfaces contacting with said sample of a torque detection die, a torque detection side fixed die and a seal plate are fixed with respect to rotational direction of the drive die, and a support body for supporting said seal plate is provided with a spring function capable of deflecting in a direction of changing the interfacial distance between said drive surface and said fixed surface, thereby reducing the volume of said sample chamber in accordance with a volume contraction generated in curing said sample.

9. A curing characteristics measuring method, wherein a separable sample chamber having a fixed surface and a rotation-vibrating drive surface is charged with a sample having a viscoelasticity, a torsional vibration is applied to said sample through said drive surface, and a shearing stress generated in said sample is measured as a torque through said fixed surface or part thereof, and wherein a measurement is performed while reducing the volume of said sample chamber following volume change generated in a curing process of said sample;

wherein said measurement is performed while changing the volume of said sample chamber by moving at least one of said drive surface and said fixed surface in a direction to change interfacial distance between both surfaces;

said sample is contacted with a rotation-drive surface of a drive die, surfaces contacting with said sample of a torque detection die, a torque detection side fixed die and a seal plate are fixed with respect to rotational direction of the drive die, and a support body for supporting said seal plate is provided with a spring function capable of deflecting in a direction of changing the interfacial distance between said drive surface and said fixed surface, thereby reducing volume of said sample chamber in accordance with a volume contraction generated in curing said sample; and said movement is achieved using air pressure as a drive source.

10. A curing characteristics measuring method, wherein a separable sample chamber having a fixed surface and a rotation-vibrating drive surface is charged with a sample having a viscoelasticity, a torsional vibration is applied to said sample through said drive surface, and a shearing stress generated in said sample is measured as a torque through said fixed surface or part thereof, and wherein a measurement is performed while reducing the volume of said sample chamber following volume change generated in a curing process of said sample;

wherein said measurement is performed while changing volume of said sample chamber by moving at least one of said drive surface and said fixed surface in a direction to change interfacial distance between both surfaces; said sample is contacted with a rotation-drive drive surface of a drive die, surfaces contacting with said sample of a torque detection die, a torque detection side fixed die and a seal plate are fixed with respect to rotational direction of the drive die, and a support body of supporting said seal plate is provided with a spring function capable of deflecting in a direction of changing the interfacial distance between said drive surface and said fixed surface, thereby reducing volume of said sample chamber in accordance with a volume contraction generated in curing said sample;

said movement is achieved using air pressure as a drive source; and value of said air pressure is varied according to a change in shearing stress in curing said sample.

* * * * *